(12) United States Patent
Palatzky et al.

(10) Patent No.: US 7,661,843 B2
(45) Date of Patent: Feb. 16, 2010

(54) APPARATUS FOR EMITTING LINEAR LIGHT

(75) Inventors: Roland Palatzky, Neusaess (DE); Michael Spatz, Augsburg (DE)

(73) Assignee: Texmag GmbH Vertriebsgesellschaft (CH)

( * ) Notice: Subject to any disclaimer, the term of this patent is extended or adjusted under 35 U.S.C. 154(b) by 0 days.

(21) Appl. No.: 11/540,455

(22) Filed: Sep. 29, 2006

(65) Prior Publication Data
US 2007/0159829 A1 Jul. 12, 2007

(30) Foreign Application Priority Data
Oct. 6, 2005 (DE) .................. 10 2005 047 913

(51) Int. Cl.
F21V 5/00 (2006.01)
F21V 29/00 (2006.01)
F21S 4/00 (2006.01)

(52) U.S. Cl. .................. 362/244; 362/249.02; 362/294

(58) Field of Classification Search .............. 362/373, 362/218, 294, 240, 242, 243, 246, 247, 249, 362/800, 216, 217, 219, 224, 225, 646, 244; 361/695

See application file for complete search history.

(56) References Cited

U.S. PATENT DOCUMENTS

| | | | | |
|---|---|---|---|---|
| 4,555,749 A * | 11/1985 | Rifkin et al. | .................. | 362/249 |
| 5,032,960 A * | 7/1991 | Katoh | .................. | 362/240 |
| 5,243,402 A | 9/1993 | Weber et al. | | |
| 6,154,362 A * | 11/2000 | Takahashi et al. | ............ | 361/695 |
| 6,390,652 B1 * | 5/2002 | Echito | .................. | 362/374 |
| 6,828,590 B2 * | 12/2004 | Hsiung | .................. | 257/79 |
| 6,880,952 B2 | 4/2005 | Kiraly et al. | | |
| 6,964,507 B2 * | 11/2005 | Mohacsi | .................. | 362/545 |
| 7,064,674 B2 * | 6/2006 | Pederson | .................. | 340/815.45 |
| 7,080,933 B2 * | 7/2006 | Chen et al. | .................. | 362/616 |
| 7,207,692 B1 * | 4/2007 | Hulse | .................. | 362/231 |
| 7,359,192 B2 * | 4/2008 | Yang et al. | .................. | 361/695 |

(Continued)

FOREIGN PATENT DOCUMENTS

CH 690 471 9/2000

(Continued)

OTHER PUBLICATIONS

Patent Office of the People's Republic of China Notification of the First Office Action for Application No. 200610142048.1 dated Jan. 9, 2009.

(Continued)

*Primary Examiner*—Ismael Negron
*Assistant Examiner*—David R Crowe
(74) *Attorney, Agent, or Firm*—Fish & Richardson P.C.

(57) ABSTRACT

The present invention relates to an apparatus for emitting light, comprising linearly arranged devices for radiating light. According to the invention, modular elements are provided which carry the devices for radiating light. The modular elements each carry one device for radiating light and can each be installed and replaced separately in the apparatus for emitting light. This facilitates simpler maintenance of the apparatus. According to a further aspect of the invention, a cooling system is provided to increase the life of the apparatus. According to a further aspect of the invention, a special diaphragm and a diffuser are provided in order to generate a more efficient light output or a more efficiently bundled light beam.

31 Claims, 3 Drawing Sheets

U.S. PATENT DOCUMENTS

| | | | |
|---|---|---|---|
| 7,429,186 B2 * | 9/2008 | Mrakovich et al. | 439/404 |
| 2002/0089852 A1 * | 7/2002 | Casciani et al. | 362/290 |
| 2002/0114155 A1 * | 8/2002 | Katogi et al. | 362/219 |
| 2004/0120152 A1 * | 6/2004 | Bolta et al. | 362/294 |
| 2006/0034085 A1 * | 2/2006 | Wang et al. | 362/294 |
| 2006/0227554 A1 * | 10/2006 | Yu | 362/294 |
| 2006/0262533 A1 * | 11/2006 | Lin et al. | 362/249 |
| 2008/0164430 A1 | 7/2008 | Diederichs | |

FOREIGN PATENT DOCUMENTS

| | | |
|---|---|---|
| DE | 37 09 500 | 10/1988 |
| DE | 40 31 633 | 10/1990 |
| DE | 10 2004 014 532 | 3/2005 |
| DE | 10 2004 014 541 | 5/2005 |
| EP | 1 205 745 | 5/2002 |
| EP | 1 577 613 | 9/2005 |
| WO | 2004/006560 | 1/2004 |
| WO | WO2004/006560 | 1/2004 |

OTHER PUBLICATIONS

Summons of Oral Proceedings issued on Jul. 30, 2009 in European Application No. 06019671.4.

English translation of Summons of Oral Proceedings issued on Jul. 30, 2009 in European Application No. 06019671.4.

Supplemental Search Report issued on Feb. 13, 2009 in European Application No. 06019671.4.

English translation of Supplemental Search Report issued on Feb. 13, 2009 in European Application No. 06019671.4.

Office action issued on Jun. 12, 2006 in German Application No. 102005047913.8.

English translation of Office action issued on Jun. 12, 2006 in German Application No. 102005047913.8.

Office action issued on Oct. 26, 2006 in German Application No. 102005047913.8.

English translation of Office action issued on Oct. 26, 2006 in German Application No. 102005047913.8.

* cited by examiner

APPARATUS FOR EMITTING LINEAR LIGHT

CROSS REFERENCE TO RELATED APPLICATION

This application claims foreign priority benefits under Title 35, United States Code, §119 to German application No. 10 2005 047 913.8, filed Oct. 6, 2005.

TECHNICAL FIELD

The present invention relates to an apparatus for emitting light, comprising linearly arranged devices for radiating light. The present invention also relates to a measuring assembly comprising such an apparatus for emitting light and one or more cameras, together with a system for detecting defects and/or irregularities on a web of material that is being conveyed past along a measurement plane.

BACKGROUND

The prior art discloses systems for detecting defects and/or irregularities on a web of material being conveyed past along a measurement plane and comprising an apparatus for emitting linear light. The term "linear light" is to be understood here as meaning as bundled light that produces an illuminated line on the web of material, usually extending transversely to the web. A system of this kind can be used to inspect for example a web of paper that is being conveyed past along the measurement plane at high speed, preferably employing one or more line scan cameras to locate defects and/or irregularities (e.g. thin spots, inclusion of flies or dirt particles, etc.) by detecting differences in brightness on the web of material by the direct lighting method or the backlighting method. In the direct lighting method, both the emission apparatus and the camera are disposed on the same side of the web of material, and in the backlighting method they are on different sides of the web.

Apparatuses for emitting linear light are known for example from WO 2004/006560 and U.S. Pat. No. 6,880,952 B2.

SUMMARY

The object of the present invention is to procure an apparatus for emitting linear light or a measuring assembly that is easier to maintain.

This object is achieved by means of an apparatus according to claim 1, a measuring assembly according to claim 24 and a system according to claim 25, respectively. The dependent claims contain advantageous configurations of the invention.

According to a further aspect of the invention, the apparatus or measuring assembly is intended to have a long lifetime. According yet another aspect of the invention, the apparatus or measuring assembly is intended to have a more efficient light output or generate a more efficient bundled light beam, so that a higher light intensity is present along the targeted line on the web of material. This will also make it possible to further increase the speed of the web of material being inspected, since the light sensitivity of the camera is limited and higher speeds therefore also require higher light intensities.

According to the present invention, the apparatus for emitting light comprises a plurality of modular elements that carry linearly arranged devices for radiating light. Such a device for radiating light may include a row of LEDs. It is also possible, however, to provide the modular elements with a plurality of light guides, each of which is connected by one end to a light source and is arranged with its other end disposed linearly along a modular element.

The modular elements each carry a device for radiating light and can each be installed and replaced separately in the apparatus for emitting light. The modular elements are preferably fastened to a tie bar. Modular construction makes it is possible to correct malfunctions in a simple manner, for example if an LED or the printed circuit board(s) provided on the module to drive the LEDs are no longer operative. The use of a very large number of LEDs to increase radiation output is precisely the type of situation in which the risk of the entire apparatus failing due to the failure of a single LED is increased. In that case, a maintenance specialist can disassemble a module while the rest of the measuring assembly and the other modules and devices for radiating light remain largely in the installed state. It is preferably provided that each module is freely accessible from the outside.

It should be kept in mind that the use of LEDs complicates the design in any event, since the device for radiating light is also provided with printed circuit board(s), including a drive, a temperature regulator and a bus communication system. The use of modular construction therefore offsets the disadvantage of the more complex design.

The modular elements preferably have a shape suitable for exactly orienting the modular element inside the apparatus. In particular, stop edges or guides for exactly orienting the modular elements may be provided in the interior of the apparatus, and for example may cooperate with the tie bar and/or with stop edges or guides of the respective adjacent modular elements. This achieves the effect of enabling linear light to be produced in a simple manner with an exact orientation even after the replacement of a module, and of ensuring a seamless and bend-free optical transition from one printed circuit board to the next.

So that the light output can be increased further without causing damage to the device for radiating light, a cooling arrangement can be provided. The modular elements can for example comprise cooling fins so heat can be dissipated into the ambient air.

According to a further aspect of the invention, an apparatus for water cooling can be connected to the tie bar for carrying the modular elements, so that water can be passed through the tie bar to cool the modular elements. The modular elements can in this case abut the tie bar in such a way that the waste heat is transferred to the tie bar by thermal conduction and thus is dissipated through the water cooling system. In this way, the lifetime of the LEDs and/or the printed circuit boards can be further increased by enhanced cooling.

Additionally or alternatively, a fan for air-cooling the modular elements can be provided. An air conduction unit can in this case route the air coming from the fan past the modular elements, especially past cooling fins provided on the modular elements.

The apparatus further preferably comprises a lens system—for example one or more rod lenses—for bundling the light emanating from the devices for radiating light in order to obtain a bundled, linear light beam on the measurement plane.

According to a further aspect of the invention, provided at a distance from the lens system is a diffuser, which is arranged between the lens system and the device for radiating light. The light output on the measurement plane can be further increased if the ratio of the distance between the device for radiating light and the diffuser to the distance between the diffuser and the center of the lens system is in the range of 1:1 to 1:4, particularly 1:2 to 1:3, particularly about 3:7.

It is also advantageous if the ratio of the distance between the device for radiating light and the center of the lens system to the distance between the center of the lens system and the measurement plane is in the range of 5:3 to 5:8, particularly about 1:1.

To better orient the light beam, a diaphragm can be provided between the device for radiating light and the lens system, preferably disposed adjacent the device for radiating light and at a distance from the lens system. According to a further aspect of the invention, said diaphragm can comprise mirror plates that extend roughly in the radiation direction and are in particular arranged parallel to one another. The parallel orientation of the mirror plates makes it possible for a diaphragm function to be achieved at higher light outputs than in the case of conventional diaphragms. It is particularly advantageous in this case if the diffuser is disposed inside the diaphragm, and in particular is trapped between the mirror plates.

The present invention is explained hereinafter on the basis of preferred embodiments with reference to the appended drawings.

DETAILED DESCRIPTION

Figure 1:
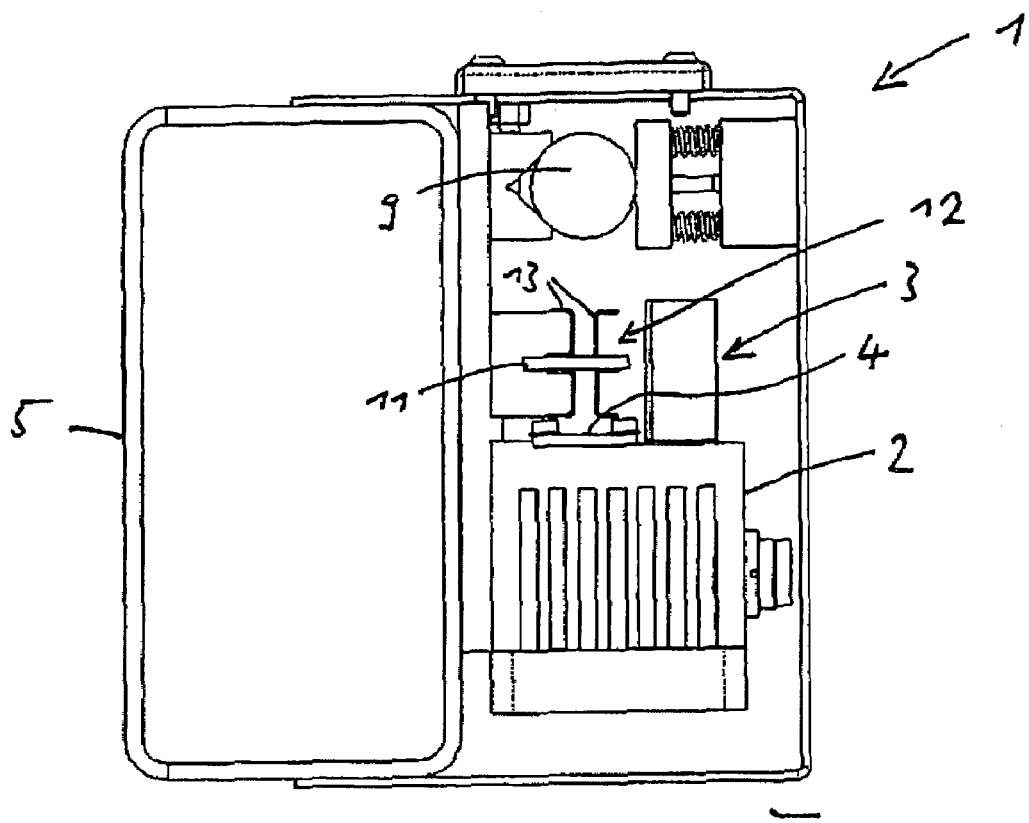
FIG. 1 shows a cross section through an apparatus for radiating light according to one embodiment of the present invention.
Figure 4:
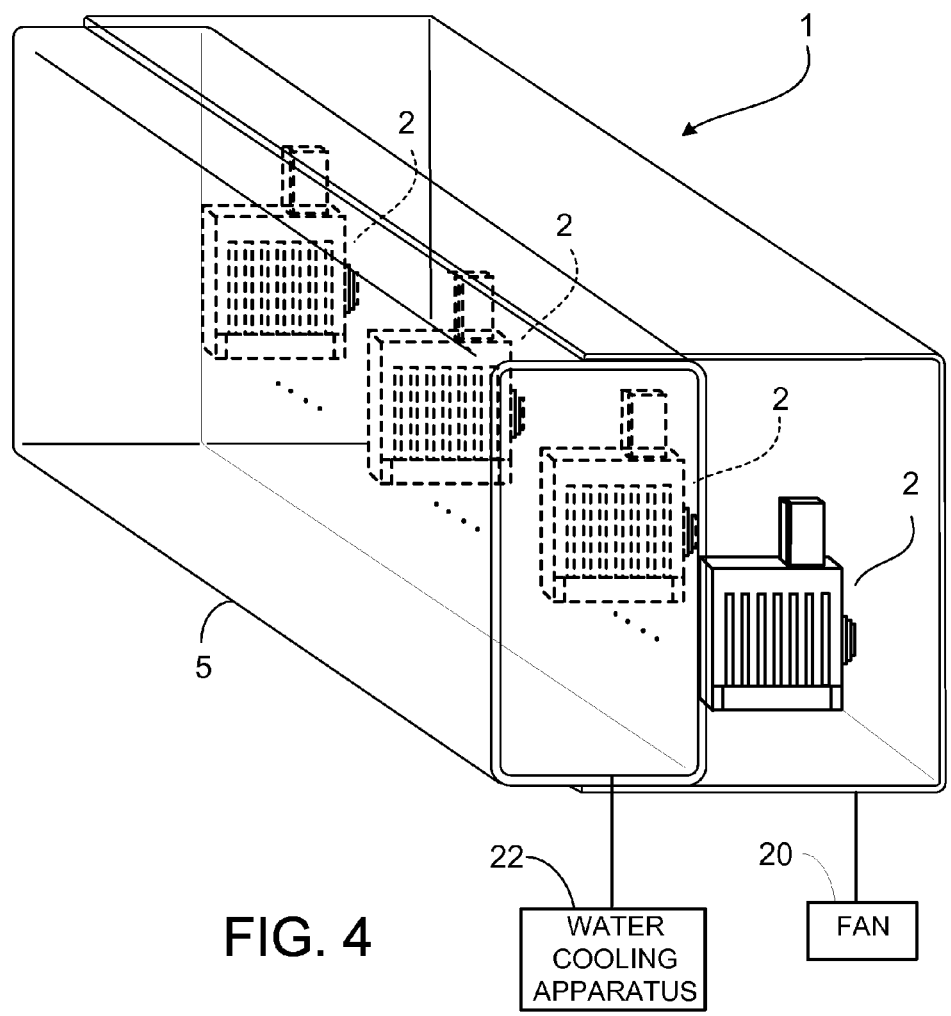
FIG. 4 shows a perspective view of an apparatus for radiating light.

FIG. 1 shows a cross section through an apparatus 1 for radiating light according to one embodiment of the present invention. FIG. 4 shows a perspective view of the apparatus 1 for radiating light. The apparatus comprises a plurality of modular elements 2, as shown in FIG. 4, which carry linearly arranged devices 3 for radiating light. Although four modular elements 2 are illustrated in FIG. 4, an apparatus can, for example, comprise 25 modular elements 2 over a length of 1 m.

Figure 2:
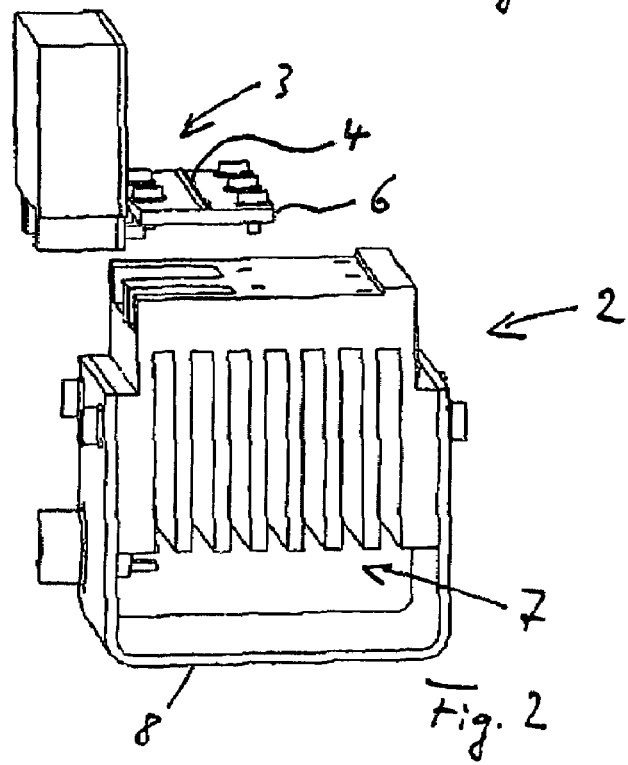
FIG. 2 shows a module according to a further embodiment of the present invention.

The device 3 for radiating light depicted in FIG. 1 and FIG. 2 includes a row of LEDs 4. However, it is also possible to provide the modular elements with a plurality of light guides, each of which is connected by one end to a light source and is arranged with its other end disposed linearly along a modular element.

The modular elements 2 each carry a device 3 for radiating light and can each be installed and replaced separately in the apparatus 1 for emitting light. The modular elements 2 are preferably fastened to a tie bar 5. Modular construction makes it possible to correct malfunctions in a simple manner, e.g. if an LED or the printed circuit board 6 provided on the module 2 to drive the LEDs is no longer operative. In that case, a maintenance specialist can disassemble a module while the rest of the measuring assembly and the other modules and devices for radiating light can remain largely in the installed state. It is preferably provided that each module is freely accessible from the outside, as is the case for example in the embodiment according to FIG. 3.

The modular elements 2 preferably have a shape suitable for exactly orienting the modular element inside the apparatus 1. In particular, stop edges or guides for exactly orienting the modular element 2 may be provided in the interior of the apparatus, and for example may cooperate with the tie bar 5 and/or with stop edges or guides of the respective adjacent modular elements. This achieves the effect of enabling linear light to be produced in a simple manner with an exact orientation even after the replacement of a module, and of ensuring a seamless and bend-free optical transition from one printed circuit board 6 to the next.

So that the light output can be increased further without causing damage to the device for radiating light, a cooling arrangement can be provided. The modular elements can for example comprise cooling fins 7 so heat can be dissipated into the ambient air.

According to a further aspect of the invention, an apparatus for water cooling 22 (see FIG. 4) can be connected to the tie bar 5 for carrying the modular elements 2, so that water can be passed through the tie bar 5 to cool the modular elements 2. The modular elements 2 can in this case abut the tie bar 5 in such a way that the waste heat is transferred to the tie bar 5 by thermal conduction and thus is dissipated through the water cooling system. In this way, the lifetime of the LEDs 4 and/or the printed circuit boards 6 can be further increased by enhanced cooling.

Additionally, or alternatively, a fan 20 for air-cooling the modular elements can be provided, as shown in FIG. 4. An air conduction unit can in this case route the air coming from the fan past the modular elements 2, especially past cooling fins 7 provided on the modular elements. Said air conduction unit can be a metal sheet 8 that surrounds the cooling fins 7.

The apparatus according to FIG. 1 further comprises a lens system 9, formed in this exemplary embodiment by a rod lens, for bundling the light emanating from the devices 3 for radiating light in order to obtain a bundled, linear light beam on the measurement plane 10.

Figure 3:
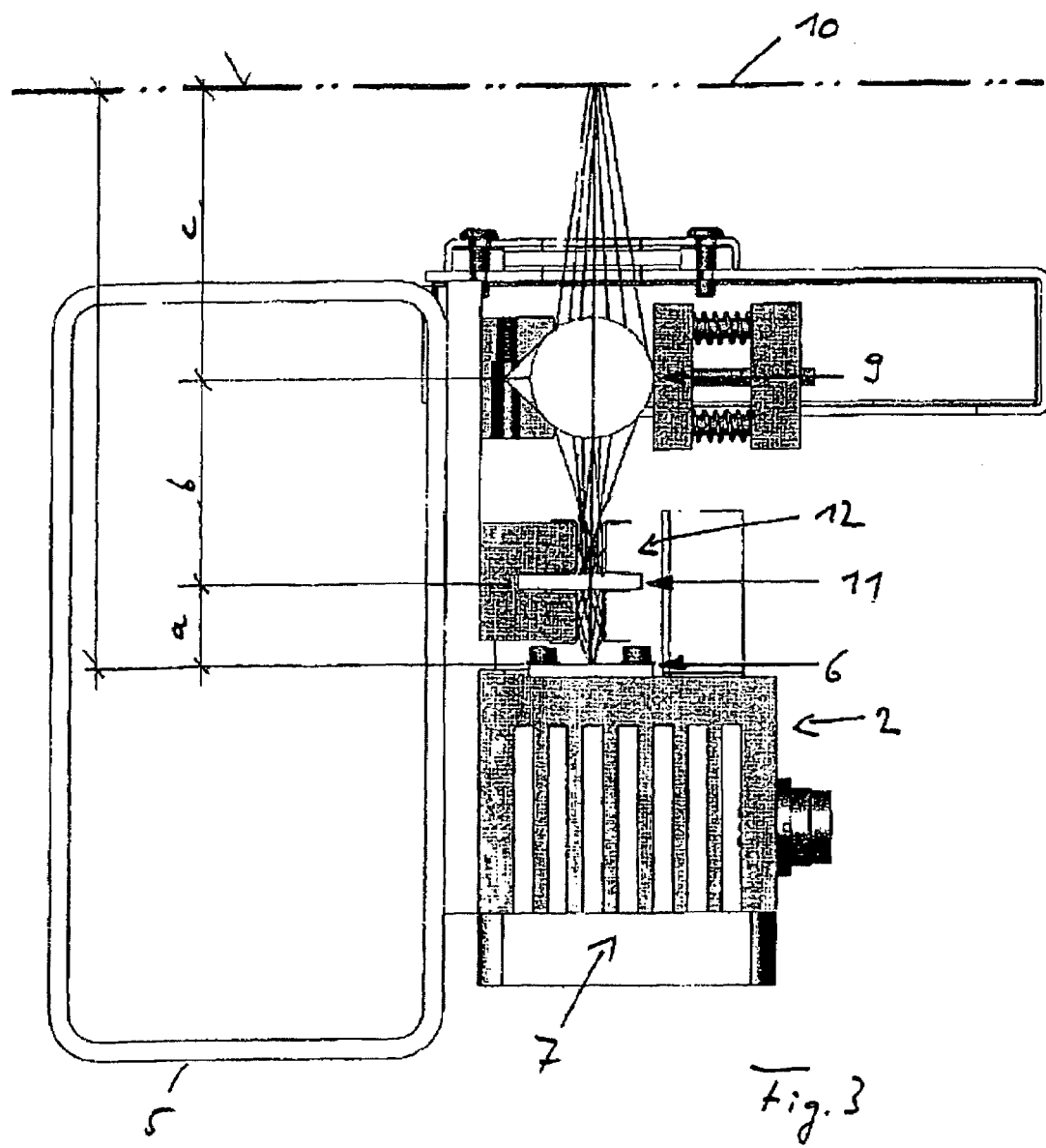
FIG. 3 shows a further cross section through an apparatus for radiating light according to a further embodiment of the present invention.

According to a further aspect of the invention, provided at a distance from the lens system 9 is a diffuser 11, which is arranged between the lens system 9 and the device 3 for radiating light. The light output on the measurement plane 10 can be further increased—as illustrated in FIG. 3—if the ratio of the distance a between the LEDs 4 of the device 3 for radiating light and the diffuser 11 to the distance b between the diffuser 11 and the center of the lens system 9 is in the range of 1:1 to 1:4, particularly 1:2 to 1:3, particularly about 3:7.

It is also advantageous if the ratio of the distance a+b between the LEDs 4 of the device 3 for radiating light and the center of the lens system 9 to the distance c between the center of the lens system 9 and the measurement plane 10 is in the range of 5:3 to 5:8, particularly about 1:1.

To better orient the light beam, a diaphragm 12 can be provided between the device 3 for radiating light and the lens system 9, preferably disposed adjacent the device 3 for radiating light and at a distance from the lens system 9. According to a further aspect of the invention, said diaphragm 12 can comprise mirror plates 13 that extend roughly in the radiation direction and are in particular arranged parallel to one another. The parallel orientation of the mirror plates 13 makes it possible for a diaphragm function to be achieved at higher light outputs than in the case of conventional diaphragms. It is particularly advantageous in this case if the diffuser 11 is disposed inside the diaphragm 12, and in particular is trapped between the mirror plates 13.

What is claimed is:

1. An apparatus, comprising:

linearly arranged devices configured to radiate light;

modular elements that each carry a respective one of the linearly arranged devices;
a tie bar; and
a lens system configured to bundle light emanating from the linearly arranged devices onto a measurement plane in order to obtain a bundled, linear light beam on the measurement plane,
wherein each modular element is replaceably fastened to the tie bar, so that each modular element can be installed and replaced separately in the apparatus;
wherein the linearly arranged devices are configured to radiate light in a radiation direction, the radiation direction being substantially parallel to a plane in which each modular element is replaceably fastened to the tie bar;
wherein each linearly arranged device comprises one or more electro-optical elements; and
wherein each modular element separately comprises:
a support base to carry the respective one of the linearly arranged devices, the support base comprising two or more cooling fins; and
an air conduction unit partially surrounding the cooling fins and being configured to convey air past the two of more cooling fins, the air conduction unit having a first end and a second end, the first end being coupled to a first side of the support base and the second end being coupled to a second, opposite side of the support base.

2. The apparatus of claim 1, wherein each linearly arranged device further comprises one or more printed circuit boards configured to drive the one or more electro-optical elements.

3. The apparatus of clam 1, further comprising:
a water cooling apparatus connected to the tie bar and configured to cool water in the tie bar so that the water can be passed through the tie bar to cool the modular elements.

4. The apparatus of claim 3, wherein the modular elements abut the tie bar such that waste heat from the modular elements is transferred to the tie bar by thermal conduction and is dissipated through the water in the tie bar.

5. The apparatus of claim 1, further comprising:
a fan configured to air-cool the modular elements.

6. The apparatus of claim 5, wherein each air conduction unit is configured to convey air coming from the fan past at least the respective modular element that comprises the air conduction unit.

7. The apparatus of claim 1, wherein the tie bar is rigid.

8. The apparatus of claim 1, wherein the lens system comprises one or more rod lenses.

9. The apparatus of claim 1, further comprising:
a diffuser, wherein the diffuser is arranged between the lens system and the linearly arranged devices, and wherein the diffuser is provided at a distance from the lens system.

10. The apparatus of claim 9, wherein a ratio of a distance (a) between at least one linearly arranged device of the linearly arranged devices and the diffuser to a distance (b) between the diffuser and a center of the lens system is in the range of 1:1 to 1:4.

11. The apparatus of claim 10, further comprising:
a diaphragm, wherein the diaphragm is arranged between the at least one linearly arranged device and the lens system.

12. The apparatus of claim 11, wherein the diaphragm is arranged adjacent the at least one linearly arranged device and at a distance from the lens system.

13. The apparatus of claim 12, wherein the diffuser is disposed inside the diaphragm.

14. The apparatus of claim 11, wherein the diaphragm comprises mirror plates that extend roughly in a radiation direction of light radiated from the at least one linearly arranged device; the radiation direction and the mirror plates being substantially parallel to the plane in which each modular element is replaceably fastened to the tie bar.

15. The apparatus of claim 14, wherein the mirror plates are arranged parallel to one another.

16. The apparatus of claim 14, wherein the diffuser is arranged between the mirror plates.

17. The apparatus of claim 1, wherein the modular elements are connected to one another via the tie bar rather than directly to one another.

18. The apparatus of claim 1, wherein, for each modular element, a cross-sectional length of the tie bar exceeds a cross-sectional width of the modular element.

19. The apparatus of claim 1, wherein each modular element is replaceably fastened to only one side of the tie bar, such that each modular element is attached to the tie bar only in a single plane, the single plane comprising the plane in which each modular element is replaceably fastened to the tie bar.

20. The apparatus of claim 1, wherein, for each modular element, the air conduction unit comprises a metal sheet.

21. The apparatus of claim 1, wherein, for each modular element, the air conduction unit of that modular element does not contact the two or more cooling fins of that modular element.

22. The apparatus of claim 1, wherein each linearly arranged device is capable of being installed and replaced separately on a respective modular element.

23. A device, comprising:
a linearly arranged device configured to radiate light, the linearly arranged device comprising one or more electro-optical elements;
a lens system configured to bundle light emanating from the linearly arranged device onto a measurement plane in order to obtain a bundled, linear light beam on the measurement plane; and
a modular element, comprising:
a support base to carry the linearly arranged device, the support base comprising two or more cooling fins; and
an air conduction unit partially surrounding the cooling fins and being configured to convey air past the two of more cooling fins, the air conduction unit having a first end and a second end, the first end being coupled to a first side of the support base and the second end being coupled to a second, opposite side of the support base;
wherein the modular element is configured to be replaceably fastened to a tie bar, so that the modular element can be installed together with other modular elements in an apparatus and can be replaced by one of the other modular elements or a different modular element; and
wherein the support base of the modular element carries the linearly arranged device such that when the modular element is replaceably fastened to the tie bar, the linearly arranged device is configured to radiate light in a radiation direction, the radiation direction being substantially parallel to a plane in which the modular element is replaceably fastened to the tie bar.

24. The device of claim 23, wherein the linearly arranged device further comprises one or more printed circuit boards configured to drive the one or more electro-optical elements.

25. The device of claim 23, wherein the air conduction unit comprises a metal sheet.

26. The device of claim 23, wherein the air conduction unit does not contact the two or more cooling fins of the support base of the modular element.

27. An illumination system for radiating light onto a web of material conveyed along a measurement plane, comprising:
- linearly arranged devices configured to radiate light onto a portion of the web of material in the measurement plane;
- modular elements that each carry a respective one of the linearly arranged devices;
- a tie bar, wherein each modular element is replaceably fastened to the tie bar, so that each modular element can be installed and replaced separately in the apparatus, wherein the linearly arranged devices are configured to radiate light in a radiation direction, the radiation direction being substantially perpendicular to the measurement plane and being substantially parallel to a plane in which each modular element is replaceably fastened to the tie bar;
- a lens system configured to bundle light emanating from the linearly arranged devices onto the portion of the web of material in the measurement plane in order to obtain a bundled, linear light beam on the portion of the web of material;
- a diaphragm, wherein the diaphragm is arranged between the modular elements and the lens system at first distance from the lens system and adjacent to the linearly arranged devices, the diaphragm comprising minor plates being arranged parallel to one another and substantially parallel to the plane in which each modular element is replaceably fastened to the tie bar; and
- a diffuser, wherein the diffuser is arranged between the modular elements and the lens system, and wherein the diffuser is provided at a second distance from the lens system, the diffuser being disposed inside the diaphragm and between the mirror plates; and
- wherein each linearly arranged device comprises:
  - one or more electro-optical elements; and
  - one or more printed circuit boards configured to drive the electro-optical elements; and
- wherein the modular elements, the linearly arranged devices, the lens system, the diaphragm, and the diffuser are all positioned on one side of the plane in which each modular element is replaceably fastened to the tie bar and the tie bar is on another side of the plane.

28. The illumination system of claim 27, further comprising:
- a housing having a first end and a second end, the first end being coupled to a first side of the tie bar and the second end being coupled to a second, opposite side of the tie bar; and
- wherein the modular elements, the lens system, the diffuser, and the diaphragm are all positioned fully within and inside the housing.

29. The illumination system of claim 27, further comprising:
- a structure attached to a first side of the tie bar and to the lens system, the structure being configured such that the structure fixedly positions the lens system relative to the tie bar and such that the modular elements are accessible from outside of the illumination system.

30. The illumination system of claim 27, further comprising:
the web of material.

31. The illumination system of claim 30, further comprising:
- a structure to convey the web of material along the measurement plane.

* * * * *

UNITED STATES PATENT AND TRADEMARK OFFICE
CERTIFICATE OF CORRECTION

PATENT NO. : 7,661,843 B2
APPLICATION NO. : 11/540455
DATED : February 16, 2010
INVENTOR(S) : Roland Palatzky and Michael Spatz It is certified that error appears in the above-identified patent and that said Letters Patent is hereby corrected as shown below:

In claim 3, column 5, line 31, please delete "clam" and insert --claim--.

In claim 4, column 5, line 37, please delete "abut" and insert --about--.

In claim 27, column 7, line 29, please delete "minor" and insert --mirror--.

Signed and Sealed this

Eighth Day of June, 2010

David J. Kappos
*Director of the United States Patent and Trademark Office*